United States Patent [19]

Zeldin et al.

[11] Patent Number: 5,442,106
[45] Date of Patent: Aug. 15, 1995

[54] PROCESS FOR HYDROLYZING ESTERS USING 4-AMINOPYRIDYL SILOXANE CATALYSTS

[75] Inventors: Martel Zeldin; Wilmer K. Fife, both of Indianapolis, Ind.; Slawomir Rubinsztajn, Schenectady, N.Y.

[73] Assignee: Indiana University Foundation, Bloomington, Ind.

[21] Appl. No.: 211,761

[22] PCT Filed: Oct. 15, 1991

[86] PCT No.: PCT/US91/07673

§ 371 Date: Apr. 15, 1994

§ 102(e) Date: Apr. 15, 1994

[87] PCT Pub. No.: WO93/08150

PCT Pub. Date: Apr. 29, 1993

[51] Int. Cl.⁶ .................. C07C 51/09; C07C 27/02
[52] U.S. Cl. .................. 562/512; 562/553; 562/579; 562/602; 562/434

[58] Field of Search ............... 562/512, 553, 579, 602, 562/434

[56] References Cited

U.S. PATENT DOCUMENTS

| | | | |
|---|---|---|---|
| 4,942,254 | 7/1990 | Young | 560/512 |
| 4,997,944 | 3/1991 | Zeldin et al. | 546/14 |
| 5,194,555 | 3/1993 | Zeldin et al. | 528/21 |

*Primary Examiner*—Johann Richter
*Assistant Examiner*—John Peabody
*Attorney, Agent, or Firm*—Woodward, Emhardt, Naughton, Moriarty & McNett

[57] ABSTRACT

Described are preferred processes for hydrolyzing activated esters using, as catalysts, siloxanes having 4-dialkylaminopyridyl groups incorporated into their polymer backbones. The preferred siloxane catalyst materials demonstrate unexpected catalytic efficacy in the hydrolysis as well as enzyme-like selectivity for ester substrates.

12 Claims, 1 Drawing Sheet

PROCESS FOR HYDROLYZING ESTERS USING 4-AMINOPYRIDYL SILOXANE CATALYSTS

BACKGROUND OF THE INVENTION

This invention resides generally in the fields of pyridine, silicon and catalyst chemistry. More particularly, it relates to the use of a siloxane having 4-dialkylamino functions incorporated into its polymer backbone as a catalyst for the hydrolysis of esters. This siloxane catalyst has shown remarkable selectivity and efficacy for the catalysis of esters, in some cases demonstrating enzyme-like substrate selectivity and catalytic efficacy.

By way of further background, 4-dialkylaminopyridines ("DAAP's") are highly nucleophilic and exhibit catalytic activity toward a variety of reactions including acylations of derivatives of carbon, phosphorous and sulfur acids, and by silylations, ester rearrangements, polymerizations, redox and other reactions. Early catalytic work with such DAAP compounds involved monomolecular species including, for instance, extensive work both commercially and in the literature with 4-dimethylaminopyridine (commonly referred to as "DMAP"). DMAP itself exhibits remarkable catalytic activity and has become a standard by which the activity of other DAAP compounds is often measured. For example, the efficacy of a subject DAAP compound in catalyzing a transacylation reaction of a sterically hindered alcohol such as 1-methylcyclohexanol with an anhydride such as acetic anhydride is commonly compared to that of DMAP. In such comparisons, the rate of the transacylation catalyzed by DMAP may be assigned a relative value of 1 (i.e., 100%), and the relative catalytic rate of the other DAAP compound is expressed as a fraction (i.e. percentage) thereof.

More recent work in this field has involved attempts to incorporate DAAP functionality into polymers while maintaining as much of its catalytic activity as possible. In so doing, the hope is that polymeric catalyst compositions may be formed which exhibit a wide range of valuable chemical, physical and dynamic-mechanical properties which prove more adaptable to varied uses than their monomeric counterparts.

For example, several vinyl-based polymeric catalysts with pendant DAAP groups have been prepared, including for instance: (1) poly[N-methyl-N-(4-vinylbenzyl)aminopyridine], Menger, F.M., McCann, D.J., J. Org. Chem. 1985, 50, 3928; (2) poly(diallylaminopyridine), Mathias, L.J., Vaidya, R.A., Bloodworth, R.H., J. Polym. Lett. Ed. 1985, 23, 147; Mathias, L.J., Vaidya, R.A., J. Am. Chem. Soc. 1986, 108, 1093; and Vaidya, R.A., Mathias, L.J., ibid 1986, 108, 5514; and (3) poly[methyl(3-styrenylpropyl)aminopyridine] crosslinked with divinylbenzene, Frechet, J.M.J., Darling, G.D., Itsuno, S., Lu, P., de Meftahi, M.N., Rolls Jr., W.A., Pure Appl. Chem. 1988, 60, 353. However, these vinyl-based catalyst materials have generally suffered in that they thermally degrade at temperatures below 300° C. and thus cannot effectively be used at higher temperatures which are preferred for many reactions. Further, in many instances the polymer-supported DAAP functions have been appended to their vinyl backbones in ways that significantly decrease their catalytic activities.

In another aspect, certain polymeric DAAP materials have been reported to exhibit high nucleophilicity in aqueous solution, although reports to this point have been quite limited. For example, only two such reports are presently known to applicant, those involving derivatives of polyethylene imine, Delaney, E.J., Wood, L.E., Klotz, I.M., J. Am. Chem. Soc. 1982, 104,799, and poly[4-(pyrrolidino)pyridines], Vaidya, R.A., Mathias, L.J., J. Am. Chem. Soc. 1986, 108, 5514.

These and other considerations have represented significant drawbacks to this point in the development of truly satisfactory polymeric catalyst materials not only having effective DAAP functionality, but also exhibiting physical, chemical and dynamic-mechanical properties which make them applicable over a wide range of reactions and reaction conditions. Additionally, in one particular aspect, the need continues for further polymeric DAAP materials which exhibit desirable properties in aqueous mediums. The applicants' invention addresses these needs.

SUMMARY OF THE INVENTION

The applicants have now discovered that siloxanes having 4-dialkylaminopyridine groups included as part of the polymer backbone, see, e.g. structure 5 below, exhibit highly unexpected and advantageous catalytic activity toward the hydrolysis of esters. Accordingly, one preferred embodiment of this invention relates to a process for hydrolyzing an activated ester. This process comprises the step of hydrolyzing the ester in an aqueous medium in the presence of a catalytic amount of a siloxane having 4-dialkylaminopyridine groups incorporated into its polymer backbone. The effective siloxane catalysts can be linear or cross-linked and homo- or copolymers, and are formed as fluids, gums, gels, elastomers or resinous materials, depending upon various factors including their degree of cross-linking, if any.

Other embodiments, objects, advantages and features of the invention will be apparent from the description which follows.

DESCRIPTION OF THE PREFERRED EMBODIMENT

Figure 1:
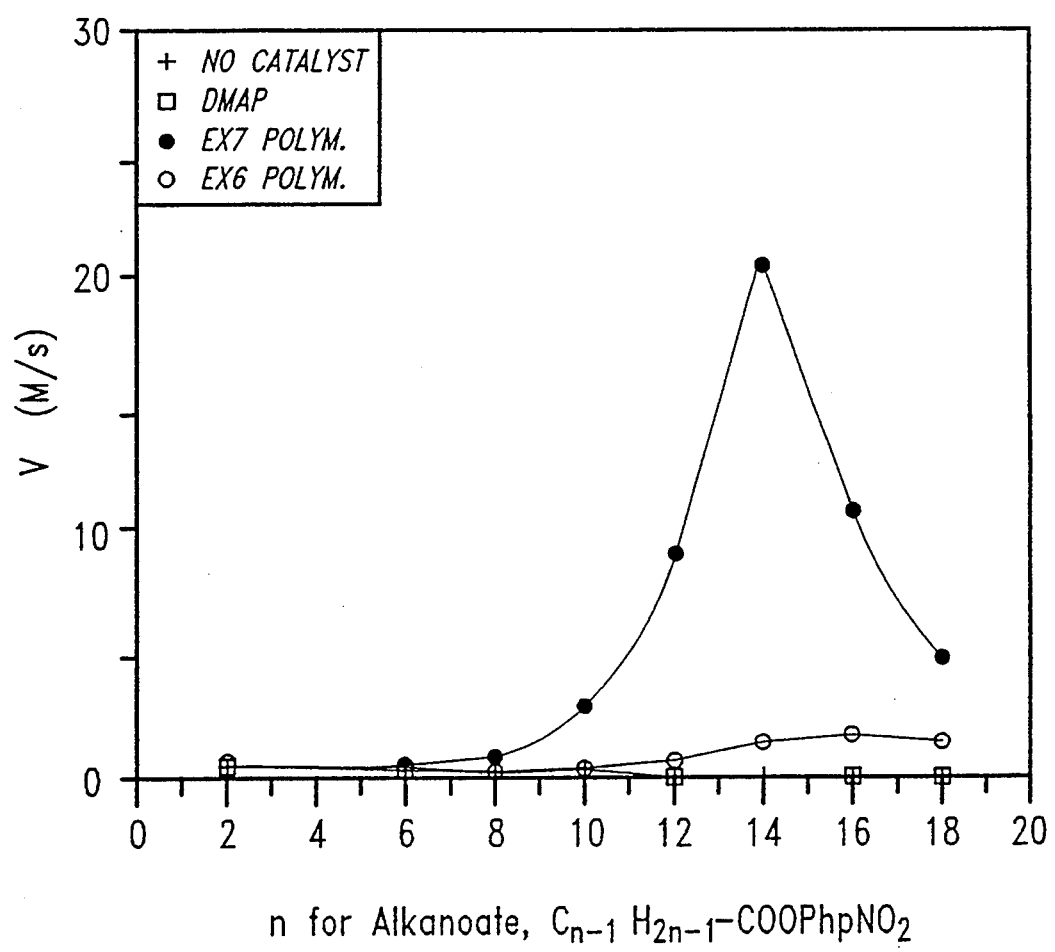

For the purposes of promoting an understanding of the principles of the invention, reference will now be made to a certain preferred embodiment and specific language will be used to describe the same. It will nevertheless be understood that no limitation of the scope of the invention is thereby intended, and that such alterations and further modifications and applications of the principles of the preferred embodiments as described herein as would normally occur to one skilled in the art to which the invention relates are contemplated as falling within the spirit and scope of the invention.

In accordance with the discussion above, one preferred embodiment of the invention relates to a process for hydrolyzing an activated ester, which process comprises the step of hydrolyzing the ester in the presence of a catalytic amount of a siloxane having 4-dialkylaminopyridine groups incorporated into its polymer backbone. As known in the art, the term "activated ester" means an ester which is susceptible to hydrolysis because of some structural feature of either its alcohol or acid portion. For example, activated esters include those which have alcohol portions which form weak bases. Representative activated esters thus include esters of para-nitrophenol, vinyl alcohol, enolpyruvate, etc. On the other hand, activated esters also include esters which have carboxylic acid portions having electronegative groups attached, particularly at the alphacarbon position. Representative activated esters thus also include esters of alpha-halogenated, alpha-hydroxylated, and alpha-aminated aliphatic carboxylic acids, to mention a few. In any event, as mentioned above, the term activated ester known in the art, is commonly used, and will be readily understood by those ordinarily skilled in the art.

It is a known and frequent practice to test a catalyst's esterase activity on para-nitrophenyl alkanoates, as summarized in Scheme I below.

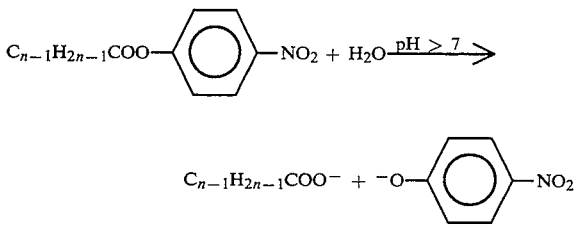

where n = an integer, typically about 3 to 30

Scheme I

As is generally accepted, the test results are then taken as a measure of the catalyst's esterase efficacy on activated esters generally. See, e.g. F.M. Menger and C.E. Portnoy, J. Am. Chem. Soc., 1967, 89, 4698; F.M. Menger and M. Laidka, J. Am. Chem. Soc., 1987, 109, 3145; and G.E. Clement and M.L. Bender, Biochemistry, 1963, 2,836. For instance, the alcohol portion of activated esters is commonly occupied by other organic groups such as those specifically mentioned above, and, generally, can include groups such as alkyl, alkenyl (e.g. vinyl or other enolate esters), aryl (mono or polynuclear), aralkyl, etc., which can be substituted or unsubstituted, and which typically have from about 1 to about 30 carbon atoms. For the instant invention, the particular organic group occupying the alcohol portion is not critical, so long as the ester as a whole is an activated ester as specified above and is soluble in the aqueous medium in which the hydrolysis is conducted. In the preferred case of alkanoate esters, a $C_8$ to $C_{20}$ alkanoate ester (i.e. in the carboxylic acid portion of the ester, $C_{n-1}H_{2n-1}COO$—, = about 8 to 20) is employed to high advantage, with $C_{12}$ to $C_{16}$ alkanoate esters, and particularly $C_{14}$ alkanoate esters, also providing highly desirable reactions, as further detailed in Example 13 below.

The process of the present invention is conducted in an aqueous medium, preferably a buffered aqueous medium exhibiting a pH of about 8 to 9. One or more suitable co-solvents will also be present to help solubilize the ester. In general, any co-solvent which is compatible with water and which provides a medium which solubilizes the ester will be suitable. Representative co-solvents thus include alcohols including lower alkyl alcohols such as methanol, ethanol, propanol, etc., as well as other water-compatible solvents such as acetonitrile, DMSO, THF, etc. The selection and use of a suitable co-solvent, and the relative amount of co-solvent to water, will be within the ability of those ordinarily skilled in the relevant art.

The siloxane polymers prepared by applicants have demonstrated remarkable thermal stability up to 375° C. and above while preserving desirable catalytic and dynamic-mechanical properties over a wide temperature range from about −100° C. to 375° C. and above. The siloxanes are thus good materials for general DAAP-type catalytic applications, far superior to their vinyl-based counterparts to date which suffer in many respects as noted above.

In accordance with the discussion above, the catalytic siloxane polymer of the invention has 4-dialkylaminopyridine functions in its backbone. In this regard, the term "siloxane" is known in the art and used herein to mean a polymer containing —Si—O—units in its backbone. Such —Si—O—units have occurred with or without other intermittent backbone structures. The preferred siloxanes used in the present invention exemplify the former type of backbone structure, and accordingly have had backbones with repeating units of —Si—R—Si—O— wherein R is a nitrogenous organic component (e.g. siloxane species 5a, 5b, 6a and 6b identified below) which includes the DAAP function. Other siloxanes which the applicants have prepared have exemplified the latter type (e.g. species 3a, 3b, 4a and 4b below). In the applicants' work thus far, these latter siloxanes have not proven to have the highly advantageous catalytic behavior towards the hydrolysis of esters as do the former siloxanes mentioned above.

As to structure and attendant physical properties, the preferred siloxanes for use in the present invention can be prepared as homo- or copolymers, linear or crosslinked, and in some instances have been end-blocked as further discussed below. These siloxanes are formed as fluids, gums, swellable gels, elastomers or resinous materials, largely depending upon the degree of their cross-linking, if any, as well their molecular weight (degree of polymerization) and other factors well known to those experienced in this area. In addition, preferred linear siloxane homo- and copolymers prepared according to the invention have been soluble in organic solvents, and have exhibited variation in molecular weights ranging from about $3 \times 10^3$ to about $1 \times 10^6$. More particularly, homopolymers thus far prepared have generally shown molecular weights less than about $1 \times 10^4$ copolymers have shown molecular weights up to about $1 \times 10^6$.

The siloxanes studied by applicants have each been prepared from a silane comprising a (i.e. at least one) 4-dialkylaminopyridine function having at least one silyl component attached to its 4-dialkylamino moiety. This silyl component is in turn functionalized with one, two or three radicals which facilitate the polymerization and/or substrate-binding process. To date, the applicants have worked with alkoxy groups in this position. However, the significance of these alkoxy or other radicals is that they functionalize the silyl component by providing a silicon bond which is labile in aqueous or other protic solvents. As is well known and understood by those skilled in this area, there are many other groups which possess this same functionalizing property and are effective substitutes for the alkoxy groups in the applicants' experiments so far. For instance, these include cycloalkoxy (e.g., —O—cylcohexyl), aralkoxy and acyloxy groups, amino groups, halo groups (preferably chloro), and many others.

Generally, the siloxane containing in-chain 4-dialkylamino pyridine groups which is used in the present invention has been prepared from a silane having two such silyl components connected to the DAAP function, and wherein each silyl component is at least monofunctional.

Accordingly, it is possible to depict silanes used by applicants thus far in the following formulas, in which silanes of the formula (2) lead to siloxane polymers usable in the present invention:

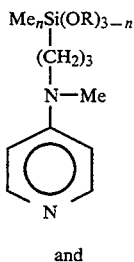

1.

and

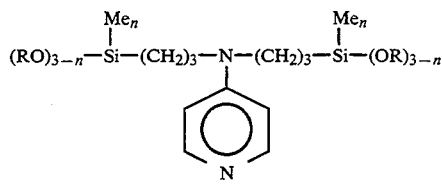

2.

wherein n=0, 1 or 2 and R to date comprises lower alkyls with methyl, ethyl, propyl and iso-propyl being preferred thus far. As those skilled in this field will appreciate, however, these only represent and define representative examples while other suitable silanes which lead to siloxanes usable within the spirit and scope of the present invention can be readily prepared with similar effective properties and being at least functional equivalents to those defined above. For instance, the spacer group separating the aminopyridyl moiety from the silicon, i.e. trimethylene [(CH$_2$)$_3$] in the formulas above, can be another organic group, including for instance a shorter or longer, branched or unbranched radical that may be an alkyl, aryl or aralkyl (i.e. benzyl) group. Such replacements are well within the knowledge and skill of those experienced in this field in view of a specific circumstance or compound under consideration.

Similarly, the methyl groups defined above can likewise be replaced with other organic groups. These include longer, branched or unbranched alkyl groups such as ethyl, propyl, iso-propyl, butyl, iso-butyl, etc., as well as aryl or aralkyl and other groups, all of which have effective properties to function within the invention as defined and claimed herein.

With the foregoing in mind, the silanes used in the applicants' studies to date according to the above formulas are as follows, with silanes 2a, 2b and 2c leading to siloxanes usable in the present invention:

| No. | Name |
|---|---|
| 1a. | N-(3-(Diethoxy(methyl)silyl)propyl)-N-methyl-4-aminopyridine |
| 1b. | N-(3-(Triethoxysilyl)propyl)-N-methyl-4-aminopyridine |
| 2a. | N,N[Bis(3-(dimethyl(ethoxy)silyl)propyl)]-4-aminopyridine |
| 2b. | N,N[Bis(3-(diethoxy(methyl)silyl)propyl)]-4-aminopyridine |
| 2c. | N,N[Bis(3-(triethoxysilyl)propyl)]-4-aminopyridine |

To date, the preferred process used to prepare these silanes has comprised the step of hydrosilating a 4-allylmethylamino- or a 4-diallylaminopyridine with an alkoxyhydrosilane (e.g. Me$_n$SiH(OR)$_{3-n}$ where n=0, 1 or 2, and R=methyl, ethyl, propyl, iso-propyl, etc.). For example, silanes have been prepared by hydrosilation of 4-(N-methylallylamino)pyridine or 4-(N-diallylamino)pyridine with triethoxysilane [(EtO)$_3$SiH], diethoxy(methyl)silane [(EtO)$_2$MeSiH] or dimethyl(ethoxy)silane [(EtO)Me$_2$SiH]. These hydrosilations have taken place upon heating the reactants in the presence of a suitable catalyst such as chloroplatinic acid or a coordination complex such as PdCl$_2$, RhCl(PPh$_3$)$_3$ or Co(CO)$_8$. Specific parameters such as catalyst and solvent selection, and reaction temperatures, pressures, and duration are often interdependent and will vary according to the specific chemistry involved. In any event, the selection and optimization of these and other parameters are well within the skills of those practiced in this area. As to preferred process conditions thus far, the applicants have conducted their hydrosilations under vacuum at temperatures and for times of about 130° C. and 10 hours, respectively. The preferred silanes have thereby been formed as colorless liquids and can be characterized by one or more of elemental analysis, infrared-, $^1$H— and $^{13}$C—NMR spectroscopy, and gas chromatography-mass spectrometry.

As discussed above, the DAAP functionality in the prepared polymers has been pendant from or incorporated into the siloxane polymer backbones, with the latter being used in the processes of the present invention. As examples, linear (i.e., 3a and 3b) and crosslinked (i.e., 4a and 4b) polymers having pendant DAAP groups have been prepared having repeating units consistent with the following formulas:

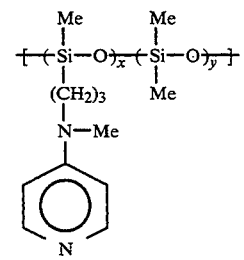

3a. x > 0, y = 0
3b. x > 0, y > 0 and

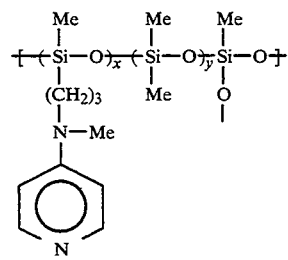

4a. x > 0, y = 0
4b. x > 0, y > 0

Preferred linear (i.e., 5a and 5b) and crosslinked (i.e., 6a and 6b) siloxane polymers having DAAP groups included within the polymer backbones have been prepared having repeating units consistent with the following formulas:

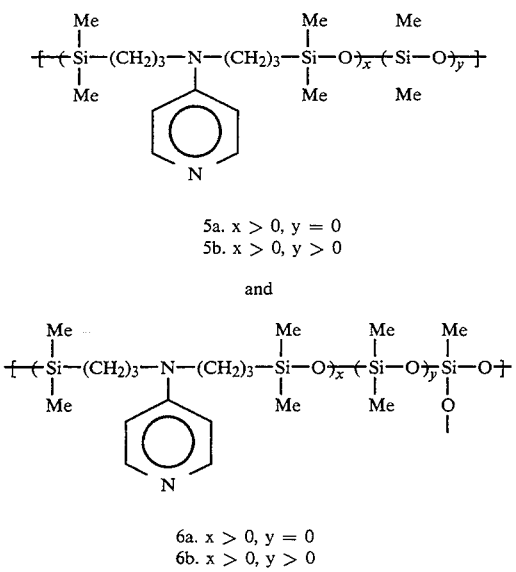

5a. x > 0, y = 0
5b. x > 0, y > 0 and 6a. x > 0, y = 0
6b. x > 0, y > 0

As to their preparation, these siloxane materials have been prepared to date by hydrolysis polymerization of a suitable silane monomer as described in detail above which includes a 4-dialkylaminopyridine function having an alkoxysilyl group attached to its 4-dialkylamino moiety. These polymerizations have occurred in the presence of a suitable base catalyst therefor as those practiced in this field will recognize. For instance, suitable catalysts for this operation generally include, but are not limited to, negatively-charged oxygen species such as hydroxide ion, which can be provided by suitable salts such as $Me_4NOH$, KOH and many others also known in the art.

As specific examples, linear siloxane homopolymers such as those of 3a and 5a above have been prepared by base-catalyzed hydrolytic polycondensations of difunctional silane monomers such as 1a and 2a above in THF/$H_2O$ mixtures. Resulting hydroxyl-terminated siloxanes may be end-blocked with a suitable end-blocking agent such as $(Me_3Si)_2O$, $(Me_3Si)_2NH$, $Me_3SiX$ (where X is a halogen such as Cl, or alkoxy such as methoxy, ethoxy, or propoxy), or bis(trimethylsilyl)acetamide. The molecular weight ($M_n$) of the polymer obtained has depended upon factors such as the monomer:catalyst ratio used, and has been determined in the Examples below using exclusion chromatography and viscosity measurements. The preferred fluid polymers of the invention are soluble in chlorinated hydrocarbons, THF and alcohols.

Copolymers such as 3b and 5b above incorporating —$Me_2SiO$—units into their polymer backbones have also been prepared by reaction of difunctional silane monomers such as 1a and 2a above either with $Me_2Si(OEt)_2$ by hydrolytic polycondensation or with linear or cyclic siloxane oligomers (e.g. $HO(SiMe_2O)_xH$, $(Me_2SiO)_3$ or $(Me_2SiO)_4$) by ring opening redistribution polymerization. As is known in the art, other linear or cyclic siloxane oligomers can be used effectively in such copolymerization procedures, where instead of the methyl groups they include other organic radicals such as longer alkyl chains (e.g. ethyl, propyl, butyl, etc), cycloalkyl, aryl or aralkyl groups. These are accordingly contemplated within the scope of the invention as described and claimed herein. Each such copolymerization method leads to high molecular weight materials, generally $M_n > 1 \times 10^5$, with the specific composition being determined by the relative quantities of reactants, the presence and amount of end-blocking agents (e.g., $(Me_3Si)_2O$), and other factors.

A variety of crosslinked materials as represented by 4a, 4b, 6a and 6b above have also been prepared. Some of these crosslinked siloxanes have been obtained by polymerization of difunctionalized DAAP-containing silanes such as those of 1a and 2a above in the presence of tri- or tetrafunctional silanes such as $Me_nSi(OEt)_{4-n}$ where n is 0 or 1, respectively. Others have been prepared by polymerization of at least trifunctional DAAP-containing silanes, for example those of 2b and 2c above, with possible inclusion of cyclic or linear dimethylsiloxyl oligomers and in the presence of these same tri- or tetrafunctional silanes. These crosslinked polymers and co-polymers have to date formed swellable gels, elastomers or insoluble resins depending upon their degrees of crosslinking and other factors. Further details as to the prepared siloxanes can be found in Examples 6-12 below.

As also indicated above, one accepted standard way to test the ability of a catalyst to effect a reaction such as a transacylation is to evaluate its efficacy in catalyzing the reaction of a sterically-hindered alcohol such as 1-methylcyclohexanol with an anhydride such as acetic anhydride. Thus, as is detailed in Example 14 and accompanying Table 3 below, several known and new DAAP materials were compared as to their rates of catalysis of this 1-methylcyclohexanol/acetic anhydride transacylation. As Table 3 evidences, the siloxanes prepared by applicants compare very favorably to the listed vinyl-based polymers with pendant DAAP functions, and consistently catalyzed this transacylation reaction at rates greater than about 75% that of DMAP, and in some instances were tested at about 80-90% or above that of DMAP.

EXAMPLE 1

Synthesis of Silane Monomer 1a:

N-(3-(Diethoxy(methyl)silyl)propyl)-N-methyl-4-aminopyridine

Silane 1a was prepared by first preparing and then hydrosilating 4-(N-methylallylamino)pyridine with diethoxy(methyl)silane, $(EtO)_2MeSiH$. The 4-(N-methylallylamino)pyridine was first obtained by reaction of 4-chloropyridine and N-methylallylamine. Thus, 4-chloropyridine (11.4 g; 0.1 mol) and N-methylallylamine (7.1 g; 0.1 mol) were combined in a glass ampoule or steel container, after which the mixture was degassed under vacuum and the vessel was sealed. The vessel was heated for three days at 130° C. The vessel was thereafter opened and the contents were dissolved in water and then neutralized with 10% aqueous NaOH. The aqueous solution was extracted with several portions of diethyl ether. The ether extract was filtered and evaporated. The residue was distilled under vacuum to give 4-(N-methylallylamino)pyridine (11.1 g; 75%; b.p. 70° C. @ 0.1 torr). 4-(N-Methylallylamino)pyridine (4.45 g; 0.030 mol), $MeSiH(OR)_2$ (6.7 g; 0.050 mol) and $H_2PtCl_6$ (60 μL; 0.080 mol/L in i-PrOH; $4.6 \times 10^{-6}$ mol) were combined and heated under vacuum in a sealed vessel for 10 hours at 130° C. Distillation of the products gave Silane 1a, N-(3-(diethoxy(methyl)silyl)propyl)-N-methyl-4-aminopyridine, as a colorless liquid (6.3 g; 74%; b.p. 122-127° C. @ 0.05 torr). The product

EXAMPLE 2

Synthesis of Silane Monomer 1b:

P

N-(3-(Triethoxysilyl)propyl)-N-methyl-4-aminopyridine

To prepare silane 1b, the procedure of Example 1 was repeated except triethoxysilane [(EtO)$_3$SiH] was used instead of the diethoxy(methyl)silane. Silane 1b, N-(3-(triethoxysilyl)propyl)-N-methyl-4-aminopyridine, was formed as a colorless liquid (40% yield, b.p. 135–140° C. @ 0.05 torr) and was characterized by elemental analysis, infrared, $^1$H and $^{13}$C—NMR spectroscopy, and gas chromatography-mass spectrometry.

EXAMPLE 3

Synthesis of Silane Monomer 2a:

N,N[bis(3-(dimethyl(ethoxy)silyl)propyl)]-4-aminopyridine

The title compound was prepared by hydrosilation of 4-diallylaminopyridine with dimethyl(ethoxy)silane, (EtO)Me$_2$SiH. The 4-diallylaminopyridine was obtained by reaction of 4-chloropyridine with diallylamine. Thus, in an experiment similar to that described in Example 1, 4-chloropyridine (11.2 g; 0.10 mol) and diallylamine (14.6 g; 0.15 mol) were combined in an ampoule, degassed under vacuum, sealed and heated for three days at 130° C. The product mixture was dissolved in water, neutralized with 10% NaOH and extracted with several portions of diethyl ether. The ether solution was filtered, the solvent was evaporated, and the residue was distilled to give 4-diallylaminopyridine (11.3 g; 65%; b.p. 92° C. @ 0.25 torr). 4-Diallylaminopyridine (5.2 g; 0.030 mol), (EtO)Me$_2$SiH (8.3 g; 0.080 mol), and H$_2$PtCl$_6$ (60 μL; 0.080 mol/L in isopropylalcohol (i—PrOH); 4.6×10 mol) were combined as in Example 1 and heated for 10 hours at 130° C. After reaction the product mixture was distilled under vacuum to give Silane 2a, N,N[bis(3-(dimethyl(ethoxy)-silyl)propyl)-4-aminopyridine, as a colorless liquid (5.75 g; 50%; b.p. 142–146° C. @ 0.05 torr), which was also characterized by elemental analysis, infrared, $^1$H and $^{13}$C—NMR spectroscopy, and gas chromatography-mass spectrometry.

EXAMPLE 4

Synthesis of Silane Monomer 2b:

N,N[Bis(3-(diethoxy(methyl)silyl)propyl)]-4-aminopyridine

The title compound was prepared by a the procedure of Example 3 except diethoxy(methyl)silane [(EtO)$_2$MeSiH] was used in the place of the dimethyl(ethoxy)silane. N,N[Bis(3-(diethoxy(methyl)silyl)propyl)-4-aminopyridine, Silane 2b, was recovered as a colorless liquid (25% yield, b.p. 164–165° C. @ 0.05 tort), and characterized by elemental analysis, infrared, $^1$H and $^{13}$C—NMR spectroscopy, and gas chromatography-mass spectrometry.

EXAMPLE 5

Synthesis of Silane Monomer 2c:

N,N[Bis(3-(triethoxysilyl)propyl]-4-aminopyridine

Silane 2c was prepared by the procedure of Example 3 except triethoxysilane [(EtO)$_3$SiH] was used instead of the dimethyl(ethoxy)silane. N,N[Bis(3-(triethoxysilyl)propyl]-4-aminopyridine, Silane 2c, was recovered as a colorless liquid (20% yield, b.p. 174–180° C. @ 0.05 torr), and characterized by elemental analysis, infrared, $^1$H and $^{13}$C—NMR spectroscopy, and gas chromatography-mass spectrometry.

EXAMPLE 6

Synthesis of Siloxane 3a:

Linear Homopolymer With Pendant DAAP Functions

To a magnetically stirred solution of Silane 1a, N-(3-(diethoxy(methyl)silyl)propyl)-N-methyl-4-aminopyridine, (1.06 g; 0.0028 mol) diluted with THF/i-PrOH (1:1 v/v, 2 mL) was added H$_2$ (99 μL; 0.0055 mol) and Me$_4$NOH (2μL; 20% in MeOH; 4.4×10$^{-6}$ mol). The mixture was stirred for 12 hours at room temperature. Volatile materials were removed by heating to 60° C. for 12 hours under vacuum. The residue was dissolved in CH$_2$Cl$_2$ (5 mL) and hexamethyldisilazane was added. The mixture was stirred at room temperature for 12 hours. Volatile materials were removed under vacuum and the polymeric product was heated under vacuum at 80° C. for 12 hours. The temperature was then raised to 140° C. for 20 minutes, The Siloxane 3a product is a pale-yellow, viscous fluid, with molecular weight dependent on the ratio of monomer-to-catalyst and conditions of reaction. Polymer 3a is soluble in CH$_2$Cl$_2$, THF, and methanol, was characterized by elemental analysis, spectroscopic methods and thermal analysis (DSC and TGA), and exhibited a T$_d$ of 375° C.

EXAMPLE 7

Synthesis of Polymer 5a:

Linear Homopolymer With DAAP Functions in Backbone

N,N[Bis(3-(dimethyl(ethoxy)silyl)propyl)-4-aminopyridine, Silane 2a, (0.85 g; 0.0030 mol) was dissolved in THF/i-PrOH (1:1 v/v, 2 mL). $_2$H O (108 μL; 0.0060 mol) and $_4$Me NOH (2 μL; 20% in MeOH; 4.4×10$^{-6}$ mol) were added and the mixture was stirred for 12 hours at room temperature. Volatile materials were removed by heating under vacuum at 60° C. for 12 hours. The resulting viscous fluid was dissolved in CH$_2$Cl$_2$ and hexamethyldisilazane (1 mL) was added. The mixture was stirred for 8 hours, then the volatile materials were removed under vacuum at 80° C. for 12 hours. The temperature was raised to 140° C. for 20 minutes. The pale-yellow, viscous polymeric 5a product has a molecular weight dependent on the ratio of monomer-to-catalyst and conditions of reaction. Siloxane 5a is soluble in CH$_2$Cl$_2$, THF, ether, toluene and methanol, was characterized by elemental analysis, spectroscopic methods and thermal analysis (DSC and TGA), and demonstrated a T$_d$ of 427° C.

EXAMPLE 8

Synthesis of Siloxane 4a:

Linear Co-polymer With Pendant DAAP Functions

N-(3-(Diethoxy(methyl)silyl)propyl)-N-methyl-4aminopyridine (Silane 1a), and cyclic polysiloxane [(Me$_2$SiO)$_3$ or (Me$_2$SiO)$_4$)] or hydroxyl terminated linear oligomer [HO(SiMe$_2$O)$_n$OH, n=less than 10] (>1 equiv), end-blocking agent (Me$_3$Si)$_2$O (<0.01 equiv.), and catalyst (Me$_4$NOH or potassium silanolate), were stirred at 60° C. for 12 hours. The mixture was then heated under vacuum at 140° C. for 6 hours. The resulting co-polymer 4b is a pale yellow viscous fluid which is soluble in organic solvents such as halogenated and aromatic hydrocarbons, and THF, and has a $T_d$ from 370° C. to 445° C. depending upon the relative quantities of the reactants and molecular weight, and to some extent of course upon the purity of the sample tested. The molecular weight of the co-polymer obtained depended on the ratio of reaction monomer and co-oligomer, and the relative quantities of (Me$_3$Si)$_2$O and catalyst.

EXAMPLE 9

Synthesis of Siloxane 5b:

Linear Co-polymer With DAAP Functions In Backbone

The procedure of Example 8 was repeated except N,N[bis(3-(dimethyl(ethoxy)silyl)propyl)-4-aminopyridine was used instead of N-(3-(diethoxy(methyl)silyl)propyl)-N-methyl-4-aminopyridine. The resulting co-polymer 5b is a pale yellow viscous fluid which is soluble in halogenated and aromatic hydrocarbons, and THF, and has a $T_d$ of 425° C. to 455° C. depending upon the relative quantities of reactants used in preparation and molecular weight, and of course to some extent upon purity. The molecular weight of the co-polymer obtained depended on the relative quantities of reactants used and the relative quantities of (Me$_3$Si)$_2$O and catalyst.

EXAMPLE 10

Synthesis of Siloxanes 4a and 6a:

Crosslinked Co-polymers With DAAP Functions Pendant From or Included in Polymer Backbone In representative experiments, N-(3-(diethoxy(methyl)silyl)propyl)-N-methyl-4-aminopyridine or N,N[bis(3-(dimethyl(ethoxy)silyl)propyl)-4-aminopyridine (Silane 1a or 2a) was dissolved in a mixture of THF and i-PrOH (1:1 v/v). Crosslinking agent [methyltriethoxysilane (0.50 equiv.)], NH$_3$(aq) (3 equiv., 6N), and Me$_4$NOH were added to the solution and the mixture was stirred for 12 hours at 60° C. Volatile materials were removed by heating the mixture at 80° C. for 12 hours under vacuum. The temperature of the residue was raised to 140° C. for 6 hours. The resulting polymer products (4a and 6a, respectively) are rubbery materials which swell in CH$_2$C$_{12}$ or THF, and have respective $T_d$'s of 460° C. and 375° C. Table 1 below summarizes these two experiments and similar experiments using varying crosslinking agent and co-monomer combinations (numbers in parentheses represent equivalents used).

TABLE 1

| Species | Monomer (mol) | Co-reactant (mol) | Crosslink, Agent (mol) | Properties |
| --- | --- | --- | --- | --- |
| 4a | 1a (1.0) | (none) | MeSi(OEt)$_3$ (0.50) | rubbery |
| 4b | 1a (1.0) | Me$_2$Si(OEt)$_2$ (1.0) | MeSi(OEt)$_3$(0.60) + Si(OEt)$_4$ (0.20) | solid resin |
| 4b | 1a (1.0) | (Me$_2$SiO)$_3$ (0.50) | MeSi(OEt)$_3$ (0.50) | solid resin |
| 6a | 2a (1.0) | (none) | MeSi(OEt)$_3$ (0.50) | rubbery |
| 6b | 2a (1.0) | (Me$_2$SiO)$_3$ (0.50) | MeSi(OEt)$_3$ (0.50) | solid resin |

EXAMPLE 11

Polymer from Silane Monomer 2b

Crosslinked Homopolymer With DAAP Functions in Backbone

A procedure analogous to that of Example 10 (except no crosslinking agent or co-reactant was added) was used to prepare a crosslinked homopolymer from silane 2b, N,N[bis(3-(diethoxy(methyl)silyl)propyl)]-4-aminopyridine. The resulting siloxane polymer is a highly crosslinked resin exhibiting good DAAP catalytic properties as illustrated in Table 3 below.

EXAMPLE 12

Polymer from Silane Monomer 1b

To a magnetically stirred solution of N-(3-(triethoxysilyl)propyl)-N-methyl-4-aminopyridine (silane 1b) (0.50g; 1.6 mmol) diluted with THF/i-PrOH (1 mL, 1:1) in a 25 mL round bottom flask under nitrogen was added NH$_3$ (aq) (90 mL; 6N) and Me$_4$NOH (2 mL; 20% in MeOH; 4.4×10$^{-6}$ mol). The mixture was stirred for temperature and then heated at 60° C. for 12 hours. Volatile materials were removed by heating at 90° C. for 12 hours under vacuum. The residue is a brown solid which is soluble in organic solvents such as CH$_2$C$_2$, CHCl$_3$ and THF. The product was dissolved in CH$_2$Cl$_2$ (5 mL) and excess hexamethyldisilazane was added. This mixture was stirred for 12 hours at ambient temperature, and the resulting polymer was reprecipitated three times from CH$_2$Cl$_2$ solution by addition of hexane. Solvents were decanted and the product was dried under vacuum for 12 hours at 90° C. The temperature was then raised to 140° C. for 20 minutes thus leaving a brown solid which is soluble in organic solvents such as CH$_2$Cl$_2$, CHCl$_3$ and THF and exhibits a $T_d$ of 400° C.

EXAMPLE 13

Hydrolysis of Organic Esters

The polymer of Example 7 was evaluated as a catalyst for hydrolysis of organic esters of alkanoic acids. Studies of this type frequently use para-nitrophenyl alkanoates as a test substrate to measure the relative efficacy of the catalyst. Accordingly, kinetic measurements were carried out as follows. Reaction mixtures were prepared in a 1.00 cm quartz cuvet. The cuvet was filled with 2.97 ml of a 1:1 mixture of methanol and aqueous buffer (0.05 M H$_2$PO$_4$/HPO$_4^-$, pH 8.0). A stock solution of catalyst in methanol (usually 5 μL) was added by microsyringe and the solution was equilibrated for 10 min. in the thermostatted cell compartment (30° plus or minus 1° C.) of a Hewlett-Packard Model 8450 spectrophotometer. An appropriate aliquot (0.03 mL) of a stock solution of para-nitrophenyl alkanoate in dioxane was added by microsyringe. The reaction mixture was quickly mixed by shaking, and the absorbance at 400 nm was recorded as a function of time. The pseudo apparent first-order rate constants were obtained as slopes of plots of $\ln[A_\infty/(A_\infty - A_t)]$ vs time, where $A_\infty$ and $A_t$ are the absorbance at infinite time and time t, respectively. Duplicate runs generally showed a measurement error of less than 5%. The data are summarized in Table 2 below, which reports the Michaelis-Menton parameters for the hydrolysis of the alkanoate ester catalyzed by the polymer of Example 7 ($2.5 \times 10^{-6}$ M) at 30° C. in 1:1 (V/V) MeOH/aqueous buffer (pH 8.0).

TABLE 2

TABLE 2

| Ester($C_n$) | $V_{max}$ (M/s) | $K_{cat}(s^{-1})$ | $K_M$ (M) | $k_{cat}/K_M(M^{-1}s^{-1})$ |
|---|---|---|---|---|
| C12 | $6.1 \times 10^{-7}$ | 0.27 | $5.9 \times 10^{-5}$ | 4,600 |
| C14 | $7.5 \times 10^{-7}$ | 0.33 | $2.9 \times 10^{-5}$ | 11,400 |
| C16 | $4.5 \times 10^{-7}$ | 0.20 | $2.4 \times 10^{-5}$ | 8,300 |

Thus, the siloxane of Example 7 not only exhibits high levels of catalytic efficiency and conforms to the Michaelis-Menten model, but also demonstrates enzyme-like specificity for esters derived from carboxylic acids of moderate chain length (e.g. about $C_{12}$ to $C_{16}$), with $C_{14}$ esters being the optimum substrate in the applicants' studies thus far.

In general, the hydrolysis of alkanoate esters ($C_2$ to $C_{18}$ acids) in the presence of 4-dimethylaminopyridine, the polymer of Example 7, the polymer of Example 6 (with pendant DAAP functions), and without catalyst was also investigated. The results are shown in FIG. 1. As can be seen, the polymer of Example 7 shows a spike from about $C_8$ to about $C_{20}$ thus demonstrating the surprising advantage of the present invention. On the other hand, the remaining experiments using 4-dimethylaminopyridine, siloxane with pendant DAAP functions, and no catalyst, exhibited no such spike or preference and not nearly the same catalytic efficacy. Other siloxanes incorporating DAAP functions into their polymer backbones, including for example Crosslinked and linear copolymers as previously described herein, demonstrate similar preference, and are also usable in the present invention.

EXAMPLE 14

Catalytic Rate in Transacylation of Sterically Hindered Alcohol and Anhydride

An accepted standard test for the ability of a catalyst to effect a transacylation is the reaction of a sterically hindered alcohol with an anhydride such as acetic anhydride. Thus, the several 4-aminopyridyl reagents listed in Table 2 were compared as described in the following experiment: Acetic anhydride (1 mL; 0.010 mol) was added with stirring to a solution which contained 1-methylcyclohexanol (0.57 g; 0.0050 mol), triethylamine (1 mL; 0.0075 mol), dodecane (0.200 mL; $8.8 \times 10$ mol) and catalyst (1 mmol). The mixture was stirred at room temperature for 17 and 31 hours. Yields of product were determined by gas-liquid chromatography and are set forth in Table 3 below.

TABLE 3

| Catalyst | Time (h) | Product Yield (%) |
|---|---|---|
| DMAP[a] | 17 | 98 |
|  | 31 | 100 |
| Poly(diallylaminopyridine)[b] | 17 | 12 |
| [hereafter Poly(diallylAP)] | 31 | 20 |
| Poly(diallyAP-co-DMAM)c | 17 | 28 |
|  | 31 | 42 |
| Siloxane 3a | 17 | 79 |
|  | 31 | 89 |
| Siloxane 5a | 17 | 83 |
|  | 31 | 91 |
| Polymer of Ex. 12 | 17 | 67 |
| (from monomer 1b) | 31 | 76 |
| Polymer of Ex. 11 | 17 | 65 |
| (from monomer 2b) | 31 | 77 |
| Polymer of Ex. 11 | 17 | 65 |
| (from monomer 2c) | 31 | 77 |

[a]4-Dimethylaminopyridine
[b]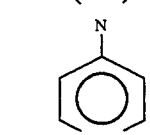
[c]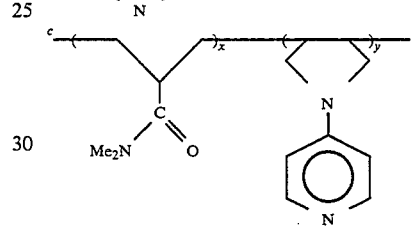

While certain preferred embodiments of the invention have been described in the forgoing description and its specific Examples, the same is to be considered as illustrative and not restrictive in character, it being understood that only the preferred embodiment has been described and that all changes and modifications that come within the spirit of the invention are desired to be protected.

What is claimed is:

1. A process for hydrolyzing an activated ester, which comprises the step of hydrolyzing the ester in an aqueous medium in the presence of a catalytic amount of a siloxane having 4-dialkylaminopyridine groups incorporated into its polymer backbone.

2. The process of claim 1 wherein the siloxane is a homopolymer.

3. The process of claim 1 wherein the siloxane is a linear polymer.

4. The process of claim 1 wherein the siloxane has a molecular weight from about 3000 to about 10,000.

5. The process of claim 1 wherein the siloxane has repeating monomeric units having the formula:

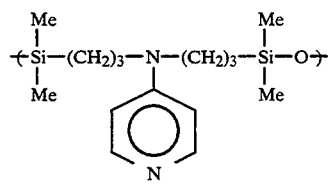

where Me=methyl.

6. The process of claim 1 wherein the ester is an alkanoate ester.

7. The process of claim 2 wherein the siloxane has repeating monomeric units having the formula:

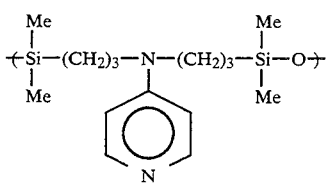

where Me=methyl.

8. The process of claim 6 wherein the siloxane has repeating monomeric units having the formula:

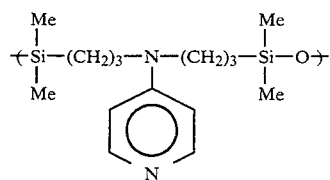

where Me - methyl.

9. The process of claim 6 wherein the ester is a $C_8$ to $C_{20}$ alkanoate ester.

10. The process of claim 9 wherein the siloxane has repeating monomeric units having the formula:

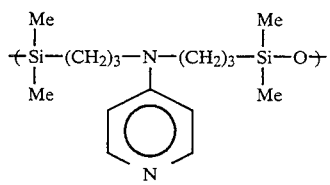

where Me=methyl.

11. The process of claim 9 wherein the alkanoate ester is a $C_{12}$ to $C_{16}$ alkanoate ester.

12. The process of claim 11 wherein the alkanoate ester is a $C_{14}$ alkanoate ester.

* * * * *

UNITED STATES PATENT AND TRADEMARK OFFICE
CERTIFICATE OF CORRECTION

PATENT NO. : 5,442,106

DATED : August 15, 1995

INVENTOR(S) : Martel Zeldin, Wilmer K. Fife and Slawomir Rubinsztajn

It is certified that error appears in the above-identified patent and that said Letters Patent is hereby corrected as shown below:

In column 9, line 8, please delete "P".

In column 9, line 44, please delete "10" and insert in lieu thereof --$10^6$--.

In column 10, line 23, please delete "$H_2$" and insert in lieu thereof --$H_2O$--.

In column 11, line 7, please delete "4aminopyridine" and insert in lieu thereof --4-aminopyridine--.

In column 11, line 61, please delete "ia" and insert in lieu thereof --1a--.

In column 12, line 2, please delete "$C_{12}$" and insert in lieu thereof --$Cl_2$--.

In column 12, line 39, after "was stirred for" please add --6 hours at room--.

In column 12, line 43, please delete "$CH_2C_2$" and insert in lieu thereof --$CH_2Cl_2$--.

In column 12, line 65, please delete "$HPO_4-$" and insert in lieu thereof --$HPO_4^-$--.

In column 13, line 64, please delete "10" and insert in lieu thereof --$10^{-4}$--.

In column 14, line 8 of Table 3, please delete "DMAM)c" and insert in lieu thereof --DMAM)$^c$--.

UNITED STATES PATENT AND TRADEMARK OFFICE
CERTIFICATE OF CORRECTION

PATENT NO. : 5,442,106
DATED : August 15, 1995
INVENTOR(S) : Martel, Zeldin, Wilmer K. Fife and Slawomir Rubinsztajn It is certified that error appears in the above-indentified patent and that said Letters Patent is hereby corrected as shown below:

In column 16, line 12, please delete "C20" and insert in lieu thereof --$C_{20}$--.

Signed and Sealed this

Fifth Day of December, 1995

BRUCE LEHMAN

*Attest:*

*Attesting Officer*   *Commissioner of Patents and Trademarks*